United States Patent [19]

Marcus et al.

[11] Patent Number: 4,812,040

[45] Date of Patent: Mar. 14, 1989

[54] HOLLOW CATHODE PLASMA PLUME

[75] Inventors: R. Kenneth Marcus; W. W. Harrison, both of Charlottesville, Va.

[73] Assignee: The University of Virginia Alumni Patents Foundation, Charlottesville, Va.

[21] Appl. No.: 31,212

[22] Filed: Mar. 27, 1987

Related U.S. Application Data

[63] Continuation of Ser. No. 725,348, Apr. 19, 1985, abandoned.

[51] Int. Cl.$^4$ ................................................. G01J 3/10
[52] U.S. Cl. ..................................... 356/314; 313/339; 250/288; 250/423 R
[58] Field of Search ................ 356/316, 314; 313/339; 250/288, 423 A, 425

[56] References Cited

PUBLICATIONS

Daughtrey et al., Analytical Chemistry, vol. 47, No. 7, Jun. 1975, pp. 1024–1028.

Harrison et al., Analytical Chemistry, vol. 46, No. 3, Mar. 1974, pp. 461–464.

*Primary Examiner*—Carolyn E. Fields
*Assistant Examiner*—Jack I. Berman
*Attorney, Agent, or Firm*—James C. Wray

[57] ABSTRACT

Sample material is sputtered from an orifice in a disc mounted in a hollow cathode. A plasma plume is ejected from the orifice and the material sputtered from the smaple is transported directly into the base of the plasma plume. Collisions with particles in the plasma plume excite the sputtered material. Light emission and absorption from the plume are measured and ions in the plume are measured. A chamber surrounding the plasma plume is maintained at about 1 torr. About 15 cc's per minute of argon are supplied to the hollow cathode at 2 torr. The power supply supplies about 200 volts at about 0.10 amps. Low energy argon ions strike the disc at the end of the cathode tube and sputter atoms off the aperture. Atoms collide with particles in the plasma causing excitation, photon emission and ionization of atoms which are measured by optical and mass spectrometers.

5 Claims, 2 Drawing Sheets

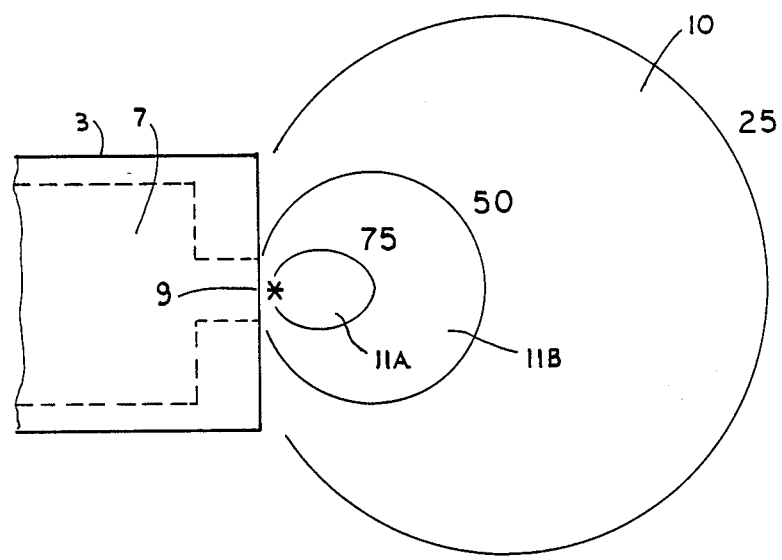
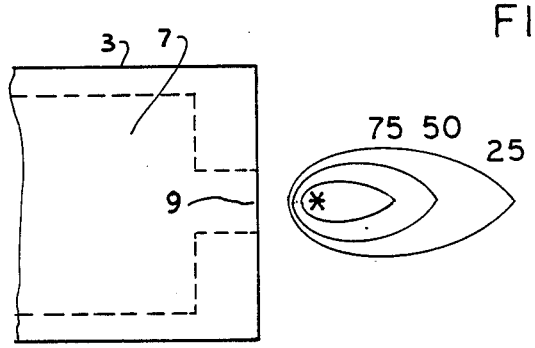
FIG. 4
FIG. 5
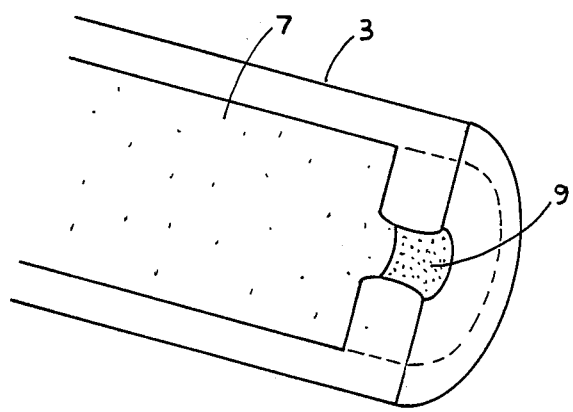
FIG. 6

HOLLOW CATHODE PLASMA PLUME

This is a continuation of application Ser. No. 06/725,348, filed April 19, 1985, now abandoned.

BACKGROUND OF THE INVENTION

The invention relates to electric lamp and discharge devices having fluent material supply or flow directing means wherein a plasma is generated of the glow discharge type. The invention also relates to systems of electric lamp and discharge devices having discharge device load with fluent material supply to the discharge space wherein a plasma is generated.

Examples of analytical plasma generating systems are present in the background art, but problems exist minimizing the value of such instruments in the analytical chemistry field, particularly in the area of elemental analysis of solids. The plasma jet electric arc was described in 1957 [*Scientific American*, 197(2) 80, 1957], but the conditions in which this device is to be used is much different than for the present invention. The inductively coupled plasma was described in 1974 [*Analytical Chemistry*, 46(13), 1155A, 1974], and is the system presently accepted in the field of analytical chemistry. Both the plasma jet electric arc and the inductively coupled plasma are suited primarily for analysis of substances in solution and not for solids.

The present invention solves the problem of placing the analyte in solution by omitting this step and analyzing the solid material directly. The invention provides a much simpler, cheaper and easier to operate system.

SUMMARY OF THE INVENTION

The invention is a hollow cathode plasma plume and method of use. Essentially, a rare gas is caused to flow through the hollow cathode chamber having a glow discharge. The gas is ionized and the ions of this rare gas strike the distal cathode base where the material to be analyzed is located and sample atoms are sputtered from the surface. The sputtered atoms are swept through an orifice located at the distal base into a plume where they collide with electrons, ions and energetic particles, causing excitation and ionization to occur. The sample atoms may be measured by optical emission or absorption through quartz windows or by mass spectrometric analysis of the ion population sampled when the ions exit through another orifice.

The invention's method begins by creating low energy argon ions. This is accomplished by imposing a voltage of about 250 volts between an anode and a cathode with a current of about 1-200 mA. Argon gas is released at a flow rate of about 10-20 cubic cm per minute. The argon gas is allowed to flow into a longitudinal bore in the cathode whereupon the argon is ionized by the applied potential. The cathode is essentially a hollow cylinder with the proximal end being the point where the argon gas is introduced and the distal end of the hollow cathode being the place where the analyte in the shape of a disc having an orifice is placed. The argon gas is flowed into the cathode, where it is ionized and then it flows towards the distal end of the cathode where it impinges upon the disc and exits the hollow cathode through the orifice in the disc and into the chamber beyond which is maintained at a pressure of about 1-10 torr. The argon gas which is ionized by the electrical potential between the anode and cathode is a plasma which protrudes into the chamber beyond the disc orifice and is maintained in the shape of a plume much akin to the flare of a candle. The plasma is considered a state of matter in which, owing to elevated temperature or electric field, atoms have been broken down to form free electrons and ions. The disc located at the distal end of the hollow cathode will have materials sputtered off the disc in the area near the orifice of the disc where the ionized argon contacts the disc and is flowed into the chamber beyond. This sputtered material consists of atoms of the disc material which are swept into the plume formed on the chamber side of the orifice. The sputtered material is swept into the base of the plume where the plasma is allowed to excite and ionize the sputtered material. This excitation-ionization consists of allowing the sputtered material to be collided with the particles comprising the plasma. Such particles can include ions, electrons, and metastable atoms. Once the sputtered material is excited and ionized in the plasma, analysis can take place. The excited sputtered material releases photons which may be analyzed through a quartz window located in the plasma chamber. This analysis would be of the atomic emission type. Atomic absorption analysis could also be carried out. The sputtered material may also be channeled through another orifice in the plasma chamber and directed into a mass spectrometer where further analysis of the ion population may take place.

The invention comprises an apparatus wherein the foregoing method may be utilized. The apparatus includes means for releasing a fluid, preferably argon gas, which is released at a flow rate in the range of 1-140 cubic cm per minute and usually 15 cubic cm per minute.

The argon gas flows to means for ionizing the fluid comprising a hollow cathode which is shaped into a cylinder. An anode is positioned adjacent the gas applied and the cathode, and a power supply is connected to the anode and cathode. The power supply introduces about 250V at a current of 0.01-1 amp and preferably 0.2 amps between the anode and cathode. The gas passing into the cathode is ionized by this energy.

The ionized gas flows through the hollow cathode to means for supporting a sample of material to be analyzed. Essentially, a sample disc having an orifice extending therethrough with the diameter approximately 1.5 mm is supported in the opposite end of the hollow cathode from where the gas is introduced. The orifice of the disc is surrounded by the analyte. It should be noted that this disc may be press fit in the hollow cathode tube or be the hollow cathode itself.

The ionized gas is directed upon the orifice of the disc, and upon contact with the disc, sputters material around the orifice whereupon the sputtered material is carried through the orifice by the ionized gas. The emerging ionized argon and sputtered material form a plasma plume. The plasma plume is surrounded by a chamber having energy transmitting windows located thereon, which is evacuated by means for evacuating.

Means for analyzing the plasma plume is attached or adjacent to the chamber. The means for analyzing the plasma plume may be an atomic absorption spectrometer, an atomic emission spectrometer, and any spectrometer suited to analyzing photon energy.

Another exit orifice may be included on the chamber allowing ionized material to exit and be introduced into mass spectrometric analytical equipment.

It is an object of this invention to provide an instrument which has multiple function capability amenable for atomic emission, mass spectrometry, atomic absorption or atomic fluorescence analysis.

It is also an object of this invention to provide for direct analysis of solids or solution residues.

It is another object of this invention to provide a simple and reliable apparatus and method for elemental analysis of solids in analytical chemistry.

It is still another object of this invention to provide an efficient apparatus and method for sample atomization and transport. For instance, in the preferred embodiment, the sample is atomized only one mm away from the plume.

It is yet another object of this invention to provide a low energy stable discharge.

Another object of the invention is to provide an analytical method comprising, creating low energy argon ions, flowing the ions towards an orifice, striking material in the orifice, sputtering the struck material, flowing sputtered material from the orifice into a plasma in a chamber beyond the orifice, exciting sputtered material in the plasma by colliding the sputtered material with particles in the plasma, and analyzing the plasma, wherein the colliding comprises colliding the sputtered material with metastable gas particles.

BRIEF DESCRIPTION OF THE DRAWINGS

FIG. 4 is a diagrammatic presentation of the relative absorbance profiles of copper atoms at 327.4 nm in the plume source. Contours drawn shown the fall off in absorbance to 75, 50, and 25% of the absorbant maximum (*).

FIG. 5 is a similar diagrammatic presentation to FIG. 4. Relative emission profiles with maximum and contours drawn as in (a). Copper cathode, 2 torr argon, 45 mA.

FIG. 6 is a diagrammatic presentation of the sputter erosion observed in the plume orifice.

DESCRIPTION OF THE PREFERRED EMBODIMENT

The invention is a simple and reliable device which permits the direct analysis of metals, alloys, etc. with respect to their elemental composition. Samples are analyzed directly in the solid state with little or no pretreatment. Such analyses provide not only qualitative (specifically, what elements are present), but also quantative (e.g., percent composition, or parts-per-million) information. This device is suited for both atomic emission and absorption, atomic fluorescence, as well as atomic mass spectrometry since significant populations of ground state and excited state atoms and singly charged ions are produced.

Figure 1:
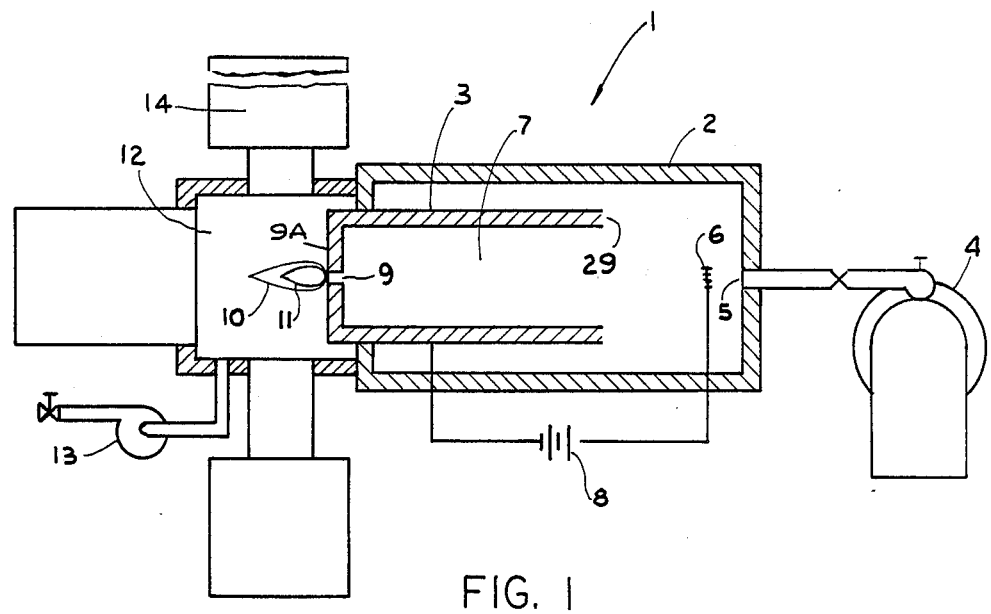
FIG. 1 is a schematic side view of the apparatus.

FIG. 1 presents a diagrammatic view of the invention. The invention is generally referred to by the numeral 1. The apparatus has a gas supply 4 which supplies a rare gas, preferably argon, through entrance port 5. Entrance port 5 is located upon a glass ceramic sleeve 2 which acts as a shield for cathode 3. The glass ceramic sleeve is cooled by tap water passing through stainless steel tubing wrapped around the sleeve. The glass sleeve insulates the entire assembly from the discharge. The hollow cathode 3 is mounted within the ceramic sleeve 2 which in turn is coupled to six-way cross 14.

The hollow cathode 3 is opened at end 29 which allows for the introduction of gas which flows through the chamber 7 towards orifice 9 located at the opposite end of the hollow cathode from the gas supply 4. Anode 6 is situated adjacent the gas supply orifice 5 and cathode 3. Power supply 8 supplies electricity to anode 6 and cathode 3. The argon gas passing through orifice 5 and by anode 6 is ionized by the potential established between the anode and the cathode. The ionized gas then flows into and through chamber 7 where it is channeled through orifice 9 creating plume 10 in chamber 12. The ionized gas is represented on the plume as areas 10 and 11. Areas 11 of the plume contain sputtered material drawn into the plume from the surrounding area adjacent to orifice 9. The sputtered material is the result of ionized gas hitting the orifice. Chamber 12 is maintained at a low pressure by evacuating means 13. Chamber 12 is preferably housed within a stainless steel 6-way cross (Norcal Products Co., Yreka Calif.). Nevertheless, other housings are conceivable and newer, simpler designs are being reduced to practice. This type housing allows the mounting of windows for optical monitoring of the discharge, as well as convenient ports for source evacuation and pressure monitoring.

Figure 2:
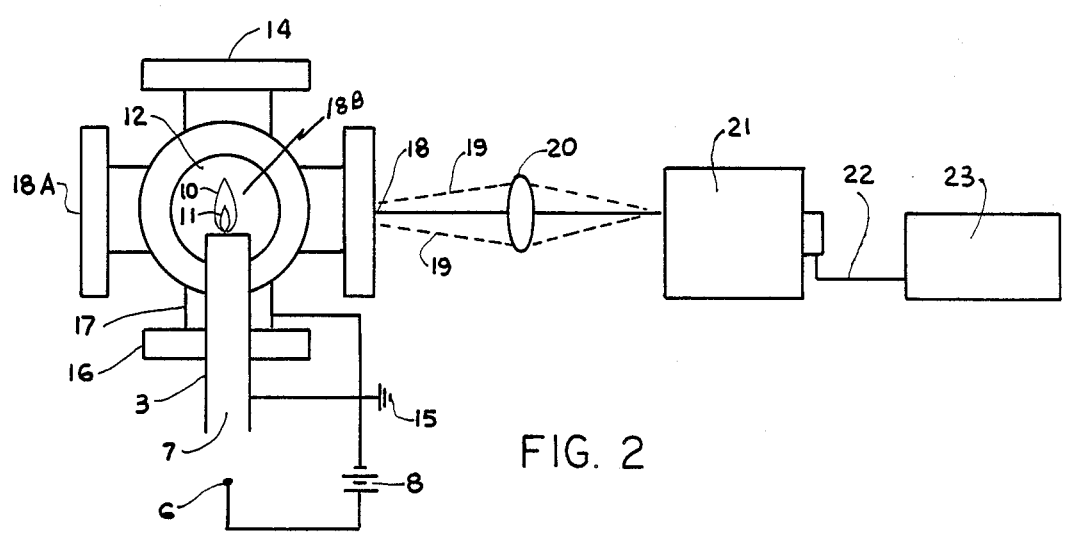
FIG. 2 is a schematic diagram of how the hollow cathode plume is used as an emission source.
Figure 3:
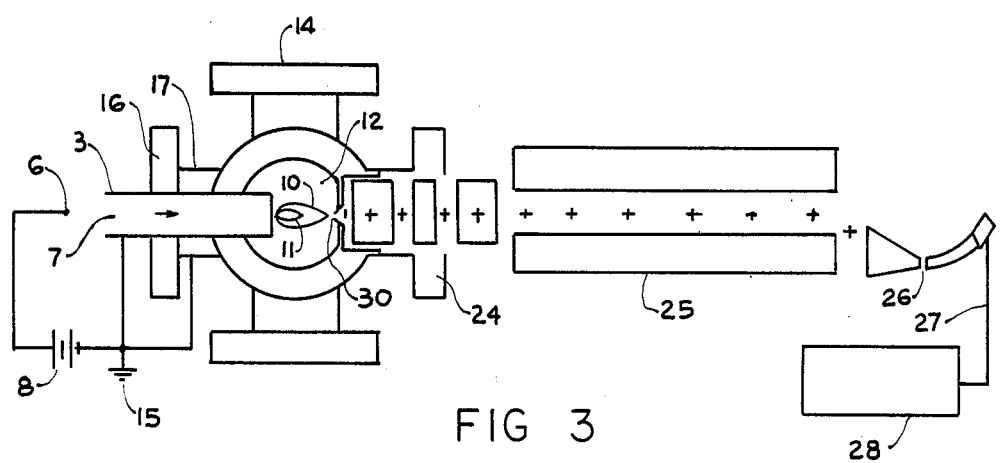
FIG. 3 is a schematic presentation of the hollow cathode plume as an ion source.

FIGS. 2 and 3 disclose diagrammatically how the invention may be used. The discharge operation is identical in both modes. A glow discharge is incorporated in a hollow cylindrical cathode 3 which serves as the first chamber of the device. A rare gas, usually argon, flows through the chamber 7 and is ionized by the discharge. Appropriate adjustment of discharge conditions causes the establishment of a high intensity plasma plume 10 in the analyzer chamber 12. Argon ions striking the cathode base 9A, principally near the plume orifice, sputter sample atoms from the cathode surface. These released atoms are swept into the plume 10 where they collide with electrons, ions, and other particles, causing excitation and ionization to occur.

These sample atoms may be measured by optical monitoring of the released photons as in FIG. 2. According to FIG. 2, light waves 19 exit window 18 whereupon lens 20 focuses light rays 19 onto monochromator 21 which selects the desired wave length of light to be measured. This light wave energy emission is converted to electrical energy and transmitted down trunk line 22 to strip chart or read out 23. The system as depicted in FIG. 2 is primarily a light emission measuring set up. However, the invention contemplates atomic absorption and atomic fluorescence set-ups as well. For example, it can be conceived that a particular light wave may be transmitted through a window located at 18A where the light may travel through chamber 12 and plasma plume 10 and out window 18. The light coming out of window 18 may be focused on the monochromator 21. The absorbance of the light transmitted through window 18A, plasma plume 10 and window 18 may be determined and converted to electrical energy which is transmitted down trunk line 22 and printed out on a strip chart or some other form of read out at 23. For atomic fluorescence analysis, it may be visualized that a particular light wave, from a laser preferably, may be transmitted through a window located at 18B where the light may travel into chamber 12 and into the plasma plume 10, thereby causing excitation of atoms in the plume. The emitted photons of the excited atoms will be measured after their passage through window 18, lens 20, and monochromator 21.

Referring to FIG. 3, the invention may provide a ion source for mass spectrometric analysis. Here the plasma plume chamber is modified slightly to allow the sputered material 11 which becomes ionized in the plasma plume 10 to exit through orifice 30 and into the Einzel lens system 24. The ions would then pass into quadrupole mass filter 25 and finally to detector 26. Detector 26 converts the information to an electronic signal which is communicated down trunk line 27 to read out means 28. It should be noted that the Einzel lens system 24, the quadrupole mass filter 25, detector 26 and read out 28 are just one embodiment of any number of mass spectrometric analytical instruments for which the invention may provide an ion source.

The analyte may be prepared as the cathode itself or as a thin disc press fitted into the base at 9A (FIG. 1) in which case the cathode is preferred to be of a high purity graphite. Solution residues on the disc surface may also be analyzed. Pressed, compacted discs of powdered material in graphite may also be used. In one embodiment, hollow cathodes were machined to a 2.54 cm length, 2.49 cm depth, 0.61 cm O.D., and 0.47 cm I.D. with a 1.5 mm exit orifice drilled through the base. Disc cathodes were 4.6 mm in diameter and 0.5-2.0 mm thick. All cathodes were rinsed in dilute nitric acid, de-ionized distilled water, acetone, and then dried.

A Kepco Model BHK 1000 power supply operating in its constant current mode maintained the discharge with currents up to 200 mA at pressures of 1-10 torr.

The vacuum system comprising the evacuating means at present centers around simply an untrapped 25 l/min roughing pump to evacuate the source to about 25 microns, followed with flushing with argon to further reduce water vapor and other background contamination. Needle valves in the argon inlet line and the evacuation line permit pressure adjustment under flow conditions requiring approximately 15 cc per minute of argon.

Optical measurements, both absorption and emission, were made with a Jarrel Ash 0.5 meter Ebert monochromator and a R106 photomultiplier tube. Atomic absorption profiles were obtained by modulating the output from a commercial hollow cathode lamp with a P.A.R. model 125 mechanical light chopper operating at 260 Hz. The hollow cathode beam was focused to a 1.5 mm diameter in the analyzer chamber and then refocused on the entrance slit of the monochrometer. The photomultiplier tube signal was fed to a P.A.R. model 122 lock-in amplifier and onto a Linear Instruments strip chart recorder. Emission studies were done by focusing the image of the plasma plume onto the monochromator entrance slit.

For profile studies, both the monochromator and the optical rail which held the lenses, chopper, and hollow cathode lamp were made adjustable. The monochromator was set on a platform which allowed precise vertical and transverse movement to follow the atomic absorption beam or to move through the emission image. The optical rail was given similar mobility to profile the plasma's ground state atomic population.

When light is to be absorbed by the plasma plume, such that atomic absorption studies may take place, the light is preferably focused on the area in the plasma plume marked 11A in FIG. 4. This is the point at which maximum absorbance takes place. These spatial factors also hold true for light emission as shown in FIG. 5. That is, light which is emitted by the plasma plume is usually of greatest intensity from area 11A.

FIG. 6 shows a diagrammatic presentation of the hollow cathode where the material to be analyzed comprises the cathode. FIG. 6 shows that the material in the orifice 9 is that which is sputtered into the plume. FIG. 6 is a representation of the sputter erosion observed in the plume orifice by the hollow cathode discharge.

Referring back to FIG. 1, the preferred method of use begins by establishing a glow discharge in chamber 7. Essentially, power supply 8 supplies to the anode 6 and cathode 3 about 250 V. It is preferred that the current be in the range of 0.01-1 amp and preferably 0.2 amps. Evacuating means 13 maintains the atmosphere within chamber 7 at a range of 0.1-10 torr and usually 2 torr. A fluid supply 4 then allows an introduction of fluid at orifice 5. It is preferred that this fluid be a rare gas such as argon. The argon enters chamber 7 where it is ionized by the glow discharge and is drawn through orifice 9 into chamber 12. Preferably, the gas is released at a flow rate of approximately 1-50 cc's per minute and usually 15 cc's per minute. As the ionized gas sweeps through orifice 9, it sputters material off the orifice and sweeps it into the plume 10. The plume sweeps the sputtered material from orifice 9 into the lower part of the plume at 11. The sputtered material then is allowed to excite within the plasma atmosphere of the plume. The plasma is considered a state of matter in which, owing to elevated temperature or electric field, atoms have broken down to form free electrons and ions. It is the interaction of the particles of the plasma with the sputtered material which causes the excitation as well as ionization of the sputtered material. It is to be understood the sputtered material is the analyte. The excitation and ionization of the sputtered material provides the phenomena which are measurable and used in analytical procedures.

Referring to FIG. 2, light which is emitted by the excitation of the sputtered material in the plume 10, is transmitted to windows located on the six-way cross type chamber 14 at 18. The light rays are focused by lens 20 onto a monochromator and photomultiplier 21 which converts the measured light wave into an electronic signal transmitted down line 22 to read out means 23.

Instead of evacuation means 13 in FIG. 1, evacuation means may be located at point 30 in FIG. 3 such that ionized sputtered material may be introduced into a mass spectrometer analytical apparatus as shown in FIG. 3.

The above described invention and method has many advantages. There is multifunction capability such that atomic absorption, atomic emission, atomic fluorescence and mass spectrometry may be performed using the invention.

The invention provides an analytical tool for direct solids analysis. For instance, the plume offers direct bulk analysis of metals, requiring no sample dilution or dissolution.

The invention provides an efficient sputter sampling. The sputter atomization is general and nonspecific such that sputter yields for most elements fall within a narrow range, an advantage for multielement analysis.

The invention provides sensitivity. The sensitivity permits the analysis of major, minor, and trace elements. The mass spectral mode provides isotopic analysis of metals and nonmetals.

The invention provides source simplicity. The plasma plume is a stable, easily controlled discharge of low current and voltage. It is quiet in operation, both electrically and audibly.

The invention is economical.

The invention is inexpensive to build and maintain. It has low power requirements. The costs of discharge gas, significant with some emission sources, are trivial due to the low flow rate. The environment of the plume is inert. There is no solution aspiration and concomitant introduction of oxidizing gases, such as water vapor. Metal oxide formation is minimized.

The invention is adaptable. It is conceivable the invention can adapt to many analytical modes, just a few of which have been described hereinabove.

Having described our invention's preferred embodiments and preferred methods of use with particularity, we now describe the spirit and scope of the invention as set out in the following claims.

What I claim is:

1. An analytical method comprising,
    flowing gas through an inlet port over an anode and into an open proximal end of a hollow cathode,
    ionizing a gas in the hollow cathode and passing the ionized gas outwardly through an orifice in a base at a distal end of the hollow cathode, the ionized gas sputtering sample material from the base near the orifice, the sputtered material and ionized gas forming a plume outside the distal end of the hollow cathode in an analyzer chamber, wherein sputtered material is ionized and excited in the plume outside of the hollow cathode, and
    optically analyzing the sample material in the plume.

2. An analytical apparatus for forming a plasma plume outside a hollow cathode and analyzing the plume comprising,
    a hollow cathode cylindrical in shape and having an open end for receiving a gas capable of being ionized, and a base at the opposite end with a central orifice providing a gas outlet, wherein sample material is disposed at the base,
    a glass sleeve having one end providing an inlet for ionizing gas and an opposite end supporting the cathode, which extends beyond the supporting end.
    an anode disposed within the glass sleeve between the gas inlet and the open end of the cathode,
    wherein gas is ionized while flowing between the anode and cathode, and wherein ionized gas passing through the central orifice of the cathode base sputters sample material from around the orifice and forms a plasma plume outside the cathode in a test chamber formed around the cathode base, and
    means, connected to the test chamber, for optically analyzing the plume.

3. The apparatus of claim 2 wherein the optical analyzing means comprises energy analyzing means connected to windows around the test chamber.

4. The apparatus of claim 2 wherein the cathode base comprises a disk having a central orifice.

5. The apparatus of claim 4 wherein the disk contains the sample material.

* * * * *